United States Patent [19]

Smalser, Sr.

[11] Patent Number: 5,754,220
[45] Date of Patent: May 19, 1998

[54] APPARATUS FOR INSPECTING THE INTERIOR OF PIPES

[75] Inventor: Paul Joseph Smalser, Sr., Hamilton, N.J.

[73] Assignee: Emerson Electric Company, St. Louis, Mo.

[21] Appl. No.: 638,174

[22] Filed: Apr. 26, 1996

[51] Int. Cl.⁶ ........................................... H04N 7/18
[52] U.S. Cl. ........................................ 348/84; 348/85
[58] Field of Search ........................ 348/84, 85, 82, 348/83, 87, 91, 92, 125–131; 354/63; 356/241; 250/256; 385/36, 119; 600/109

[56] References Cited

U.S. PATENT DOCUMENTS

| | | | |
|---|---|---|---|
| 2,994,046 | 7/1961 | Granqvist | 333/24 |
| 3,739,089 | 6/1973 | Latall | 348/84 |
| 3,758,050 | 9/1973 | Watts et al. | 243/32 |
| 3,761,623 | 9/1973 | Hara et al. | 348/84 |
| 3,832,724 | 8/1974 | Duval | 354/63 |
| 3,914,715 | 10/1975 | Hubing et al. | 333/24 |
| 4,249,810 | 2/1981 | O'Connor et al. | 354/63 |
| 4,560,931 | 12/1985 | Murakami et al. | 324/220 |
| 4,607,925 | 8/1986 | Kamigaichi et al. | 348/84 |
| 4,901,069 | 2/1990 | Veneruso | 340/853 |
| 4,991,006 | 2/1991 | Wood | 348/84 |
| 5,090,259 | 2/1992 | Shishido et al. | 348/84 |
| 5,140,265 | 8/1992 | Sakiyama et al. | 348/84 |
| 5,144,848 | 9/1992 | Uenishi et al. | 348/84 |
| 5,195,392 | 3/1993 | Moore et al. | 348/84 |
| 5,355,128 | 10/1994 | Riordan | 340/854.7 |
| 5,565,633 | 10/1996 | Wernicke | 73/865.8 |

*Primary Examiner*—Tommy P. Chin
*Assistant Examiner*—Y. Lee
*Attorney, Agent, or Firm*—Vickers, Daniels & Young

[57] ABSTRACT

Portable apparatus for inspecting the interior of a pipe comprises a battery operated television camera connected to one end of a coaxial cable which is adapted to be stored in a rotatable storage drum. The battery is mounted on the storage drum for rotation therewith and the drum is rotatably mounted on a stand. Relatively rotatable inductive coupling components are provided between the drum and stand for transmitting the camera output signal to a camera monitor such as a television receiver.

50 Claims, 7 Drawing Sheets

APPARATUS FOR INSPECTING THE INTERIOR OF PIPES

BACKGROUND OF THE INVENTION

This invention relates to the art of apparatus for inspecting the interior of pipes such as sewer lines and, more particularly, to portable apparatus including a battery operated camera for viewing and/or photographing an interior of a pipe.

Apparatus for inspecting and/or photographing the interior of pipes is known and in general, as shown for example in U.S. Pat. No. 3,832,724 to Duval, comprises a housing carrying a camera or cameras by which conditions in a pipe can be observed at a remote location and/or photographed. The housing enclosing the cameras is displaced through a pipe, and in the Duval patent such displacement is achieved by attaching opposite ends of the housing to driven winches. The camera or cameras are connected to a source of power by a cable through a cable reel or the like located exteriorly of the site to be inspected, and the camera cable at the reel is connected such as by a slip ring arrangement to the power supply and to a monitoring device by which conditions within the pipe can be observed.

Sewer line or pipe inspecting apparatus of the foregoing character advantageously enables locating cracks, root blockage, pipe breakage or cave-in and other obstructions within the interior of a pipe and further enables visual inspection or observation of the condition as well as the permanent recording of the condition such as by a film camera or the use of a VCR. Such location of a problem as well as the ability to visually observe the same advantageously facilitates the maintenance and/or pipe replacement operation necessary to alleviate the problem.

While inspection apparatus such as that shown in the patent to Duval serves its intended purpose, such apparatus heretofore available is both structurally complex, expensive and comprised of a large number of parts or components which have to be carried to and from a site to be inspected and which render setting up and operation of the apparatus both difficult and time consuming. Moreover, the apparatus is neither economically nor operationally feasible for use by an individual plumber and, accordingly, the latter generally has to use a snake to probe for and dislodge an obstruction in a sewer line or pipe. While the latter may clear an obstruction, there is no capability of determining whether conditions within the pipe require maintenance or replacement to prevent such blockage in the future. Another disadvantage attendant to sewer line inspecting apparatus heretofore available results from the fact that the slip ring arrangements necessary for transferring power between the power source and camera cable are subject to moisture and dirt contamination and thus a high rate of wear in response to the winding and unwinding of the camera cable relative to the storage reel. Accordingly, frequent maintenance and/or replacement is necessary and, in any event, there is a gradual degradation of picture quality and the potential for progressively reduced quality as a result of dirt and moisture between the slip rings.

SUMMARY OF THE INVENTION

In accordance with the present invention, apparatus for inspecting the interior of a pipe or sewer line is provided which advantageously minimizes or overcomes the foregoing and other disadvantages of apparatus heretofore available. More particularly in this respect, pipe inspecting apparatus according to the invention is portable and manually operable by a single operator and is capable of inspecting the interior of pipes having an inner diameter as small as three inches. In accordance with one aspect of the invention, a camera is provided on one end of a camera cable and is powered by a battery mounted on and rotatable with a cable storage component. The camera cable is manually extendable and retractable relative to the storage component by the operator to facilitate feeding the camera into a pipe to be inspected and withdrawing the camera following an inspection. The camera cable has an end attached to the storage component, and the battery is electrically connected to the latter end of the cable for powering the camera. The cable storage component is rotatably mounted on a support which can be carried by an operator, whereby the camera, cable and power supply is a unitary, portable assembly. The support for the cable storage component is provided with a terminal adapted to be connected to a camera monitor such as a video receiver, and a relatively rotatably signal coupling arrangement is provided between the terminal and the end of the camera cable attached to the storage component for transmitting a camera output signal to the terminal and thus to the camera monitor.

In accordance with another aspect of the invention, the relatively rotatable signal coupling arrangement includes inductively coupled conductors, one of which is connected to the fixed end of the camera cable on the storage component and the other of which is connected to the terminal on the support for the storage component. The output signal from the camera is thus transferred to the monitor without any potential for loss of image quality as the result of moisture and/or dirt between the relatively rotating conductors. Further, the spacing between the inductively coupled conductors avoids the problem of wear encountered with slip rings. Accordingly, maintenance and down time are minimized and the quality of the picture at the monitor is both optimized and remains constant over long periods of use. Importantly in connection with this aspect of the invention, mounting of the battery on the rotatable cable storage component enables powering of the camera and related circuitry and the transmission of the camera output signal to the terminal and thence across inductive coupling to the camera monitor. With the inductive coupling, a battery of practical size for the apparatus would not have sufficient power to operate the camera if the battery were mounted on the support for the storage component.

It is accordingly an outstanding object of the present invention to provide portable, battery operated camera apparatus for inspecting the interior of a pipe.

Another object is the provision of apparatus of the foregoing character comprising a camera on one end of a camera cable stored for extension and retraction on a rotatable storage component on which the battery is mounted for rotation therewith.

Still another object is the provision of apparatus of the foregoing character wherein a support for the rotatable cable storage component is provided with an output terminal connectable to a camera monitor, and the camera output signal is coupled to the output terminal by a relatively rotatable signal coupling arrangement between the output terminal and an end of the camera cable connected to the storage component.

Yet another object is the provision of apparatus of the foregoing character wherein the output terminal and the end of the camera cable attached to the storage component are inductively coupled.

Yet a further object is the provision of apparatus of the foregoing character wherein the quality of the image on the camera monitor is optimized and is consistently of the same quality.

3

Still a further object is the provision of apparatus of the foregoing character which is comprised of a minimum number of component parts structurally interrelated and of a weight facilitating carrying thereof by a single operator and wherein the camera cable is manually feedable into and from a pipe to be inspected by the operator.

Still another object is the provision of apparatus of the foregoing character which is economical to produce, requires minimum maintenance, is easy to use and is efficient in operation.

BRIEF DESCRIPTION OF THE DRAWINGS

The foregoing objects, and others, will in part be obvious and in part pointed out more fully hereinafter in conjunction with the written description of a preferred embodiment of the invention illustrated in the accompanying drawings in which.

DESCRIPTION OF A PREFERRED EMBODIMENT

Figure 1:
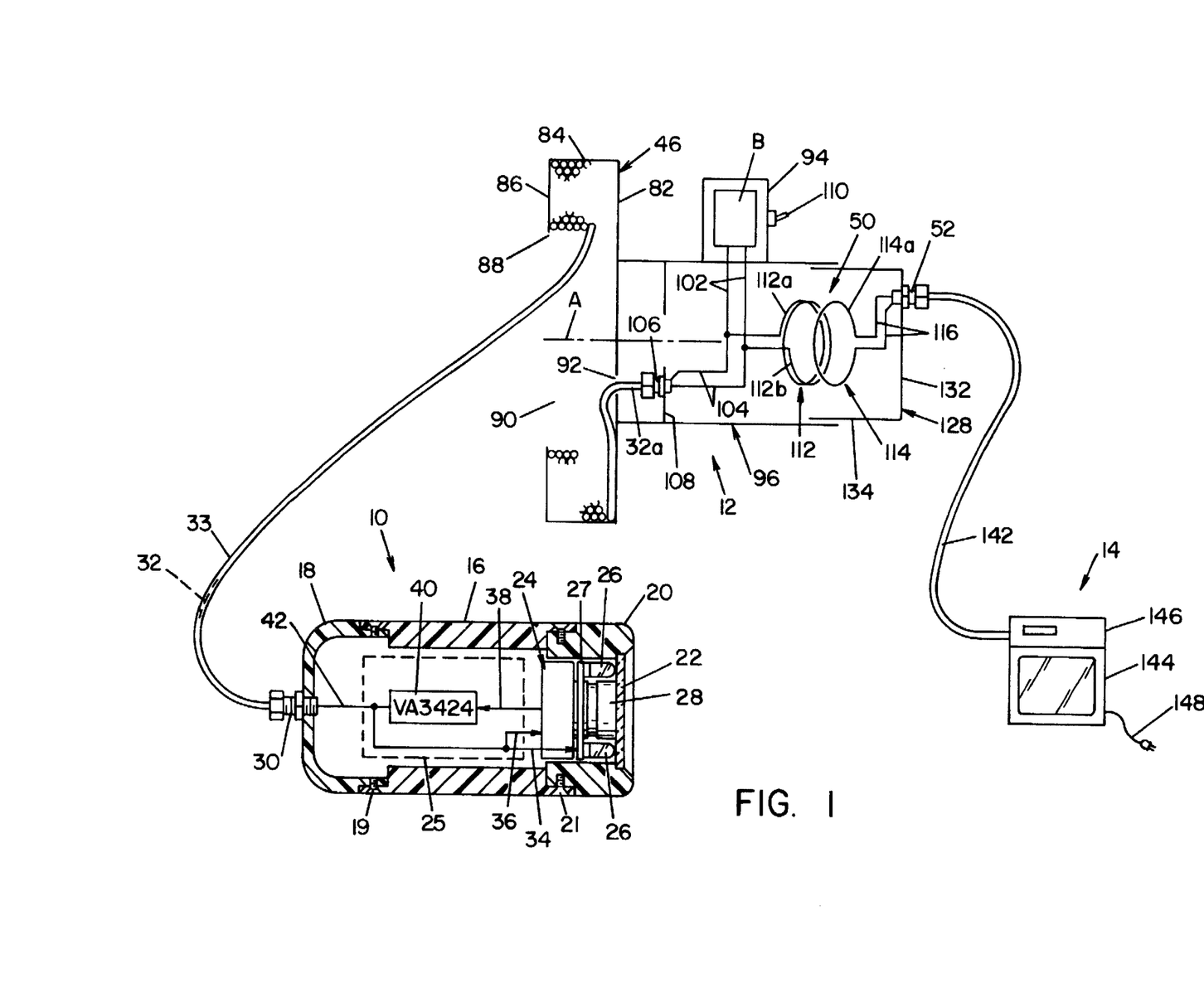
FIG. 1 is a somewhat schematic illustration of the component parts of pipe inspecting apparatus according to the invention.

Referring now in greater detail to the drawings wherein the showings are for the purpose of illustrating a preferred embodiment of the invention only, and not for the purpose of limiting the invention, pipe inspecting apparatus according to the invention comprises a camera assembly 10, a cable storage and power supply assembly 12 by which the camera in camera assembly 10 is powered to provide a camera output signal and a camera signal receiving unit 14. As best seen in FIG. 1, camera assembly 10 comprises a housing of a suitable material such as nylon and including an annular central portion 16, a rear end cap 18 and an annular front end cap 20 which supports a Lexan lens 22. Rear and front end caps 18 and 20 are removably fastened to central portion 16 by screws 19 and 21, respectively. A television camera 24 is supported in the housing adjacent the front end thereof together with a plurality of high intensity light emitting diodes 26 which are positioned laterally outwardly adjacent the camera lens 28 for lighting the interior of a pipe during an inspection operation. Rear end cap 18 of the housing is provided with a wiring connector 30 by which the camera assembly 10 is connected to cable storage and power supply assembly 12 through coaxial cable 32. More particularly in this respect, as schematically illustrated in FIG. 1 and as will be understood without description in detail from the wiring diagram in FIG. 2, camera 24 and LED's 26 are adapted to be powered by a battery B on cable storage and power supply assembly 12 through coaxial cable 32 and circuitry on component boards 25 and 27 supported in the housing of camera assembly 10. LED's 26 are mounted on component board 27 and the circuitry includes input power lines 34 and 36 to the LED's and camera 24, respectively, a camera signal output line 38 leading to a radio frequency modulator 40 on component board 25 and by which the video output signal of camera 24 is converted to a radio frequency signal which is receivable on a standard television receiver. The radio frequency signal is outputted through line 42 to the end of coaxial cable 32 which is coupled to connector 30, and the signal is transmitted to signal receiving unit 14 in the manner described more fully hereinafter.

Figure 6:
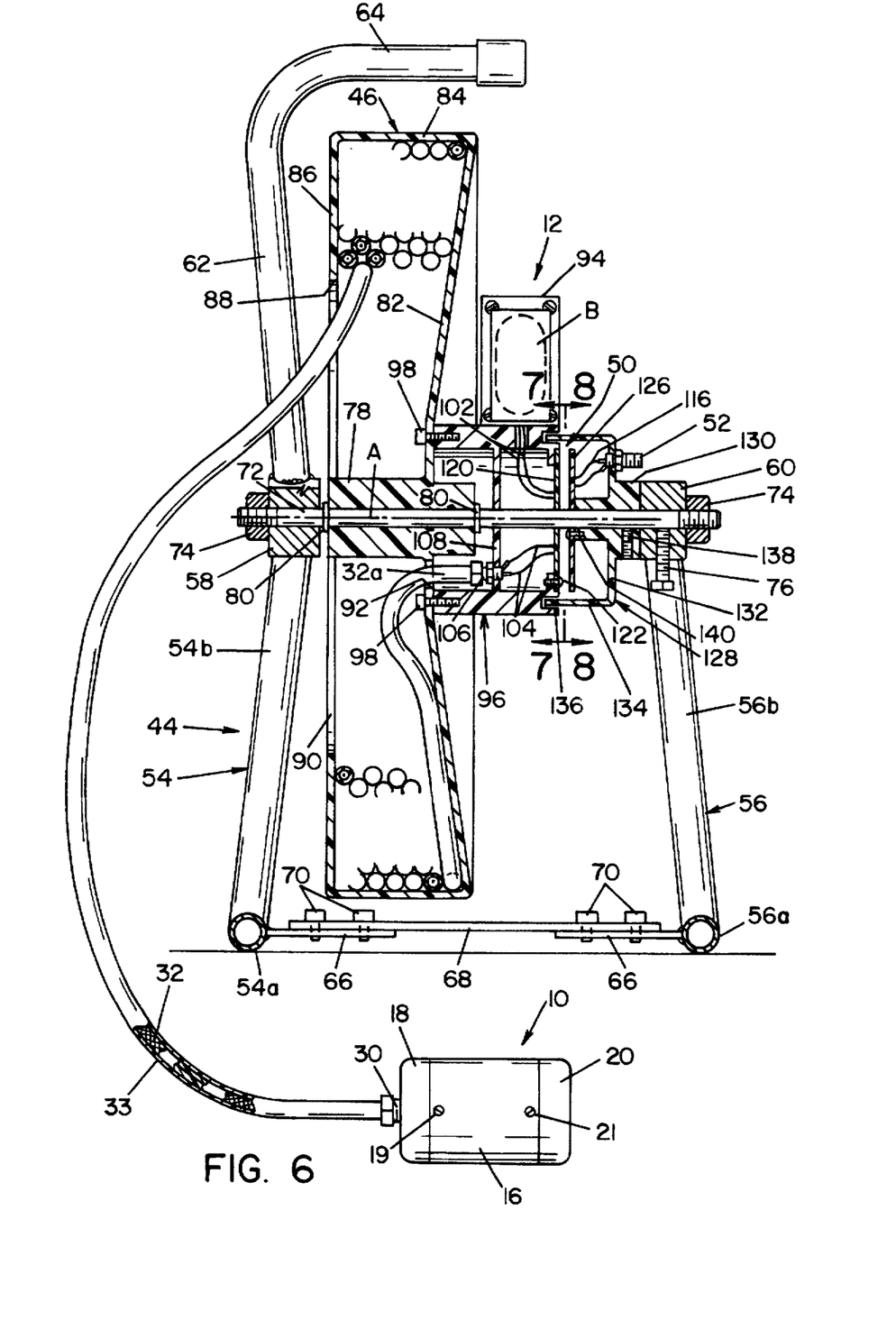
FIG. 6 is a sectional elevation view of the apparatus taken along line 6—6 in FIG. 5.

Preferably, camera 24 is a Computar EM200-L38 camera having a 3.8 mm lens. This particular camera has length, width and height dimensions of about 1.25" each which advantageously enables the camera housing to have an outer diameter of about 2", whereby the inspection apparatus is usable with pipes having an inner diameter as small as 3". As will become apparent hereinafter, camera assembly 10 is advanced into a pipe to be inspected by manually pushing coaxial cable 32 into the pipe. Preferably, as best seen in FIG. 6, coaxial cable 32 is enclosed in a fiberglass sheath 33 which extends from the end of the cable at connector 30 on camera assembly 10 to the opposite end of the cable in storage and power supply assembly 12. Sheath 33 advantageously protects the cable against abrasion during use of the apparatus and also provides stiffness to the cable against lateral flexing to facilitate pushing of the camera assembly into a pipe to be inspected.

As best seen in FIGS. 3–6, and as schematically illustrated in FIG. 1, cable storage and power supply assembly 12 comprises a stand 44, a cable storage drum 46, battery B, an inductive coupling assembly 50 and an output terminal 52. Storage drum 46 has an axis A, and stand 44 includes axially spaced apart end members 54 and 56 of steel tubing formed into a triangular configuration to provide corresponding bottom legs 54a and 56a and corresponding pairs of legs 54b and 56b extending upwardly and inwardly from the opposite ends of the corresponding bottom leg. The converging upper ends of legs 54b are welded or otherwise secured to an apertured shaft support member 58, and the converging upper ends of legs 56b are similarly connected to an apertured shaft support member 60. A carrying handle is provided by an inverted L-shaped steel tube having a leg 62 welded to and extending upwardly from shaft support member 58 and a leg 64 spaced above and extending axially across storage drum 46. Each of the bottom legs 54a and 56a is provided with a pair of straps 66 welded thereto and extending axially inwardly therefrom, and each pair of straps is interconnected by a corresponding connecting strap 68 suitable secured thereto such as by socket head bolts 70. Preferably, while not shown, straps 68 are provided with axially extending slots receiving the socket head bolts to facilitate adjusting the axial spacing between end members 54 and 56.

A storage drum shaft 72, which provides axis A, extends through shaft support members 58 and 60 and has its axially opposite ends threaded to receive nuts 74 by which the shaft is axially retained on the stand. A threaded bolt 76 extends through a threaded opening therefor in shaft support member 60, and the inner end of bolt 76 engages shaft 72 to hold the shaft against rotation relative to the stand. Storage drum 46 is supported on shaft 72 for rotation relative thereto and, in this respect, the drum includes an apertured hub 78 which receives shaft 72 and is axially positioned thereon by a pair of spring clips 80. Drum 46 further includes an axially inner side wall 82 extending radially outwardly from hub 78, a radially outer peripheral wall 84 extending axially outwardly from wall 82, and an axially outer side wall 86 extending radially inwardly from wall 84 and having a radially inner peripheral edge 88 providing an opening 90 therethrough. Drum walls 82, 84 and 86 provide an annular housing in which coaxial cable 32 is coiled between the side walls 82 and 86 and outer peripheral wall 84, and the cable has an inner end 32a which extends through an opening 92 therefor in wall 82 for connection to battery B and a component of inductive coupling 50 as set forth more fully hereinafter.

Battery B is mounted on storage drum 46 for rotation therewith about axis A by means of a battery pack housing 94 and an annular mounting sleeve 96, both of which are constructed of nylon or the like. Mounting sleeve 96 extends axially outwardly from the outer side of drum wall 82 and is secured thereto such as by threaded fasteners 98, and battery pack housing 94 is secured to the outer periphery of sleeve 96 such as by threaded fasteners 100 which extend through housing 94 and into threaded openings therefor in mounting sleeve 96. Battery B is a rechargeable battery which accordingly is removably mounted in battery pack housing 94 and, in a well-known manner, the latter has terminals for electrically contacting terminals on the battery, whereby battery power can be transmitted to the camera, radio frequency modulator and the LED's in camera assembly 10 through coaxial cable 32. As schematically illustrated for this purpose in FIGS. 1 and 6, leads 102 from the battery are connected to leads 104 having ends connected to end 32a of coaxial cable 32 through a connector 106 supported on a wall 108 interiorly of sleeve 96. Leads 104 also have ends connected to one component of inductive coupling 50 as will become apparent hereinafter. Battery pack housing 94 is provided with a switch 110 by which the circuit to leads 104 is adapted to be opened and closed. In the preferred embodiment, battery B is a 12 volt battery which provides sufficient power to drive the camera, modulator and LEDs for a period of about 8 hours over a coaxial cable length of about 100 feet.

Figure 2:
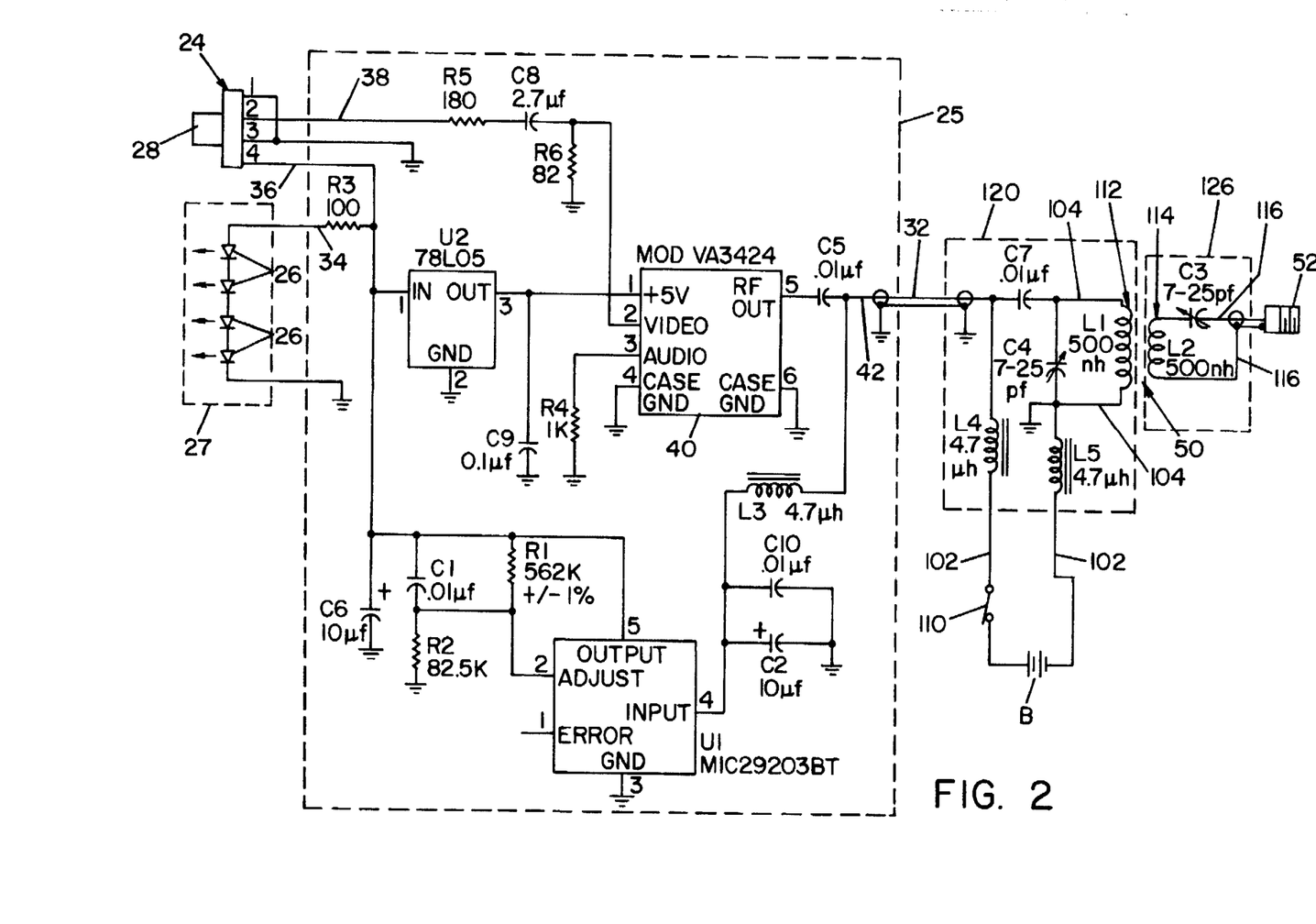
FIG. 2 is a schematic wiring diagram for the apparatus.
Figure 3:
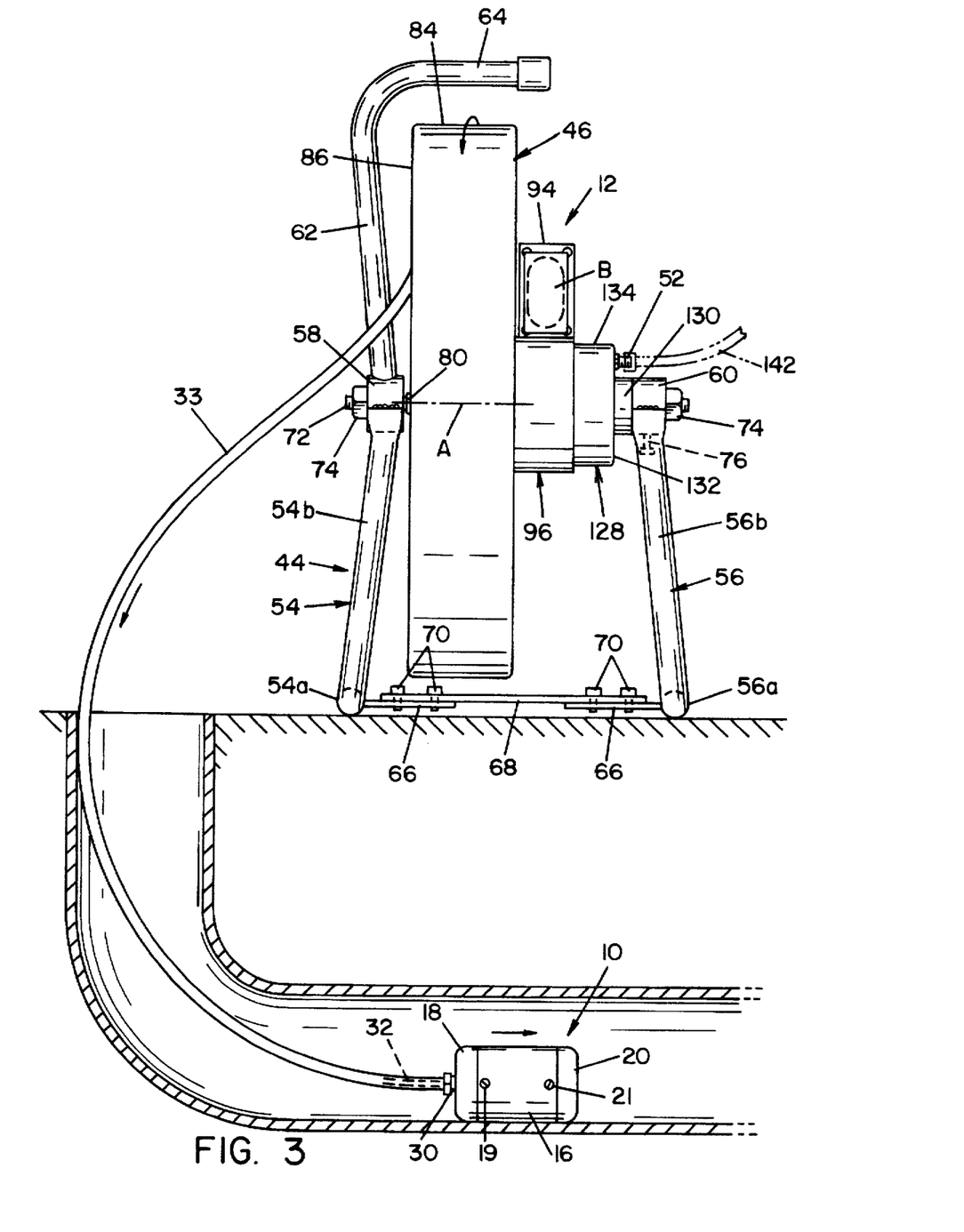
FIG. 3 is an end elevation view of the apparatus.
Figure 4:
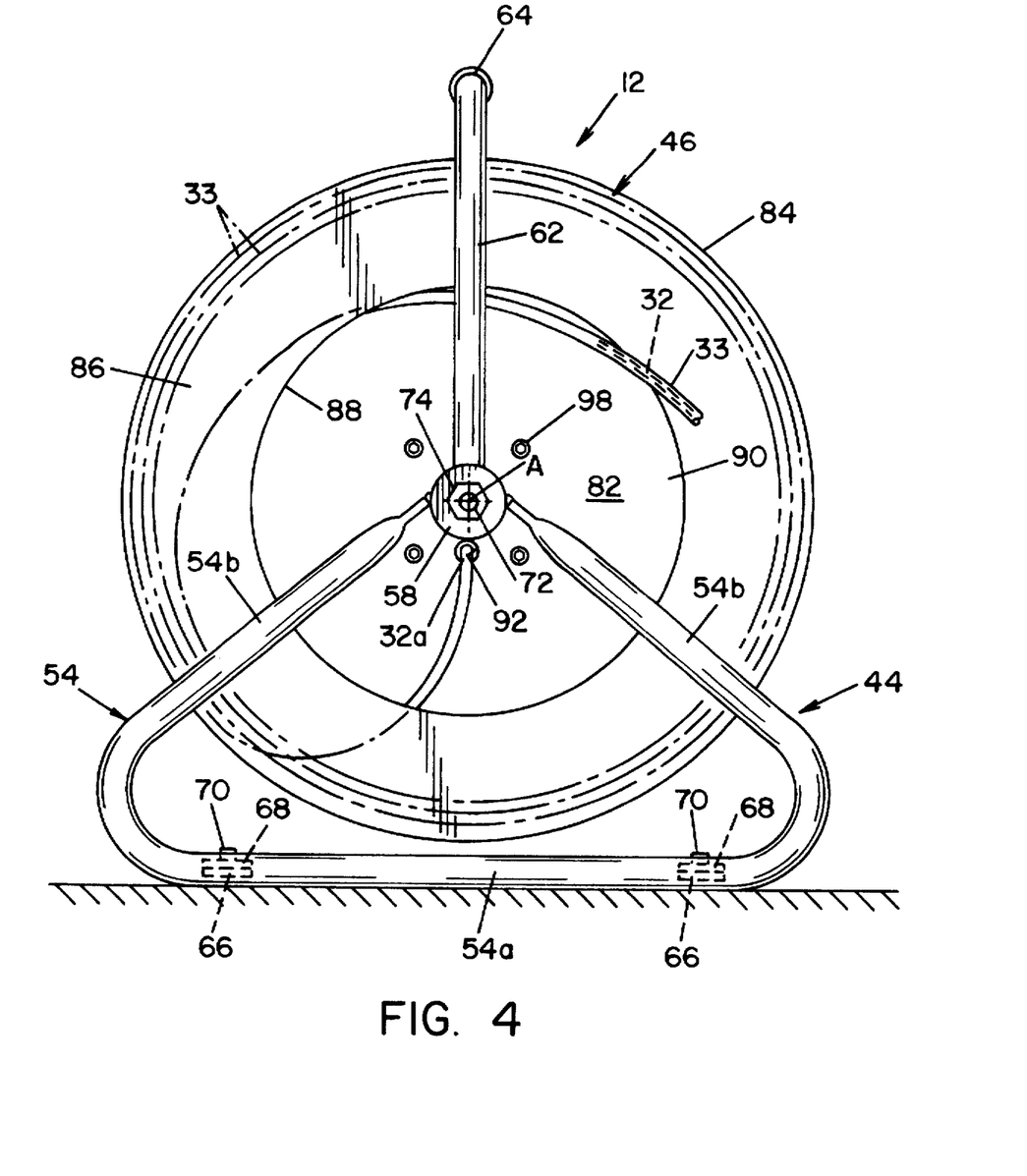
FIG. 4 is a side elevation view of the apparatus looking from left to right in FIG. 3.
Figure 5:
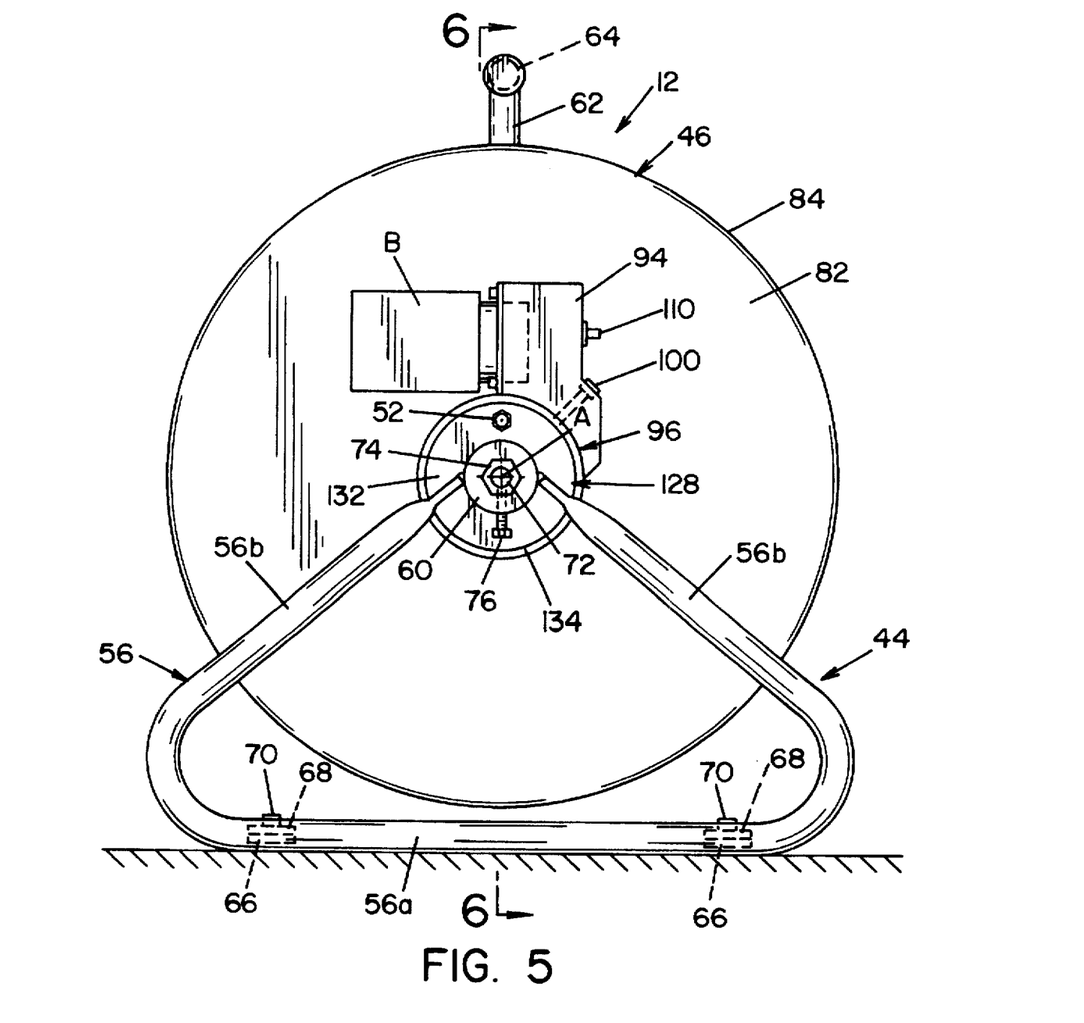
FIG. 5 is an end elevation view of the apparatus looking from right to left in FIG. 3.
Figure 7:
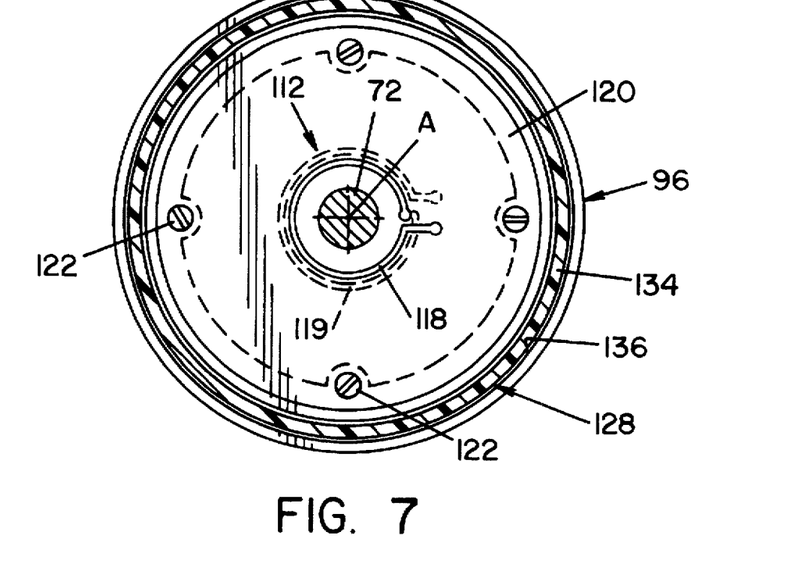
FIG. 7 is a sectional elevation view taken along line 7—7 in FIG. 6 and showing the rotatable inductive coupling component.
Figure 8:
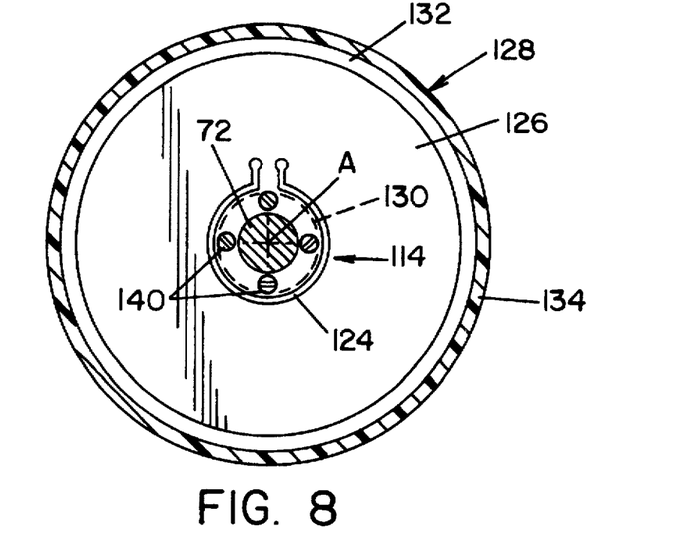
FIG. 8 is a sectional elevation view taken along line 8—8 in FIG. 6 and showing the fixed inductive coupling component.

As schematically shown in FIG. 1, and as will be appreciated from the wiring diagram of FIG. 2, inductive coupling 50 comprises primary and secondary windings 112 and 114, respectively, having corresponding resonant circuits including capacitors C4 and C3, respectively. Primary winding 112 has two turns 112a and 112b, and the ends of the winding are connected to leads 104. Winding 112 is mounted on the storage drum for rotation therewith as set forth more fully hereinafter. The ends of secondary winding 114, which has one turn 114a, are connected by leads 116 to output terminal 52 and, as will become apparent hereinafter, secondary winding 114 and output terminal 52 are mounted on shaft 72 against rotation relative thereto, whereby primary winding 112 rotates relative to secondary winding 114. Preferably, as indicated in FIG. 7, the two turns of primary winding 112 are provided by circular conductors 118 and 119 of copper clad on opposite sides of a disc 120 of epoxy impregnated class cloth. More particularly in this respect, the side of disc 120 which is visible in FIG. 7 shows conductor 118 as a solid line, and conductor 119 which is on the opposite side from that visible in FIG. 7 is shown by broken line. As will be appreciated from FIGS. 1 and 7, the clad conductors providing turns 112a and 112b are connected through disc 120 so as to be in series between the terminal ends of the winding. As shown in FIG. 8, the single turn of secondary winding 114 comprises a circular conductor 124 of copper clad on a disc 126 of epoxy impregnated glass cloth. While conductor 119 is shown in FIG. 7 as being of larger diameter than conductor 118, this is for the purpose of illustration and, preferably, circular conductors 118, 119 and 124 are all of the same diameter.

As shown in FIG. 6, disc 120 is mounted on the axially outer end of mounting sleeve 96 by a plurality of nylon screws 122 and, as will be appreciated from FIG. 7, conductors 118 and 119 are coaxial with axis A when mounted on sleeve 96. As further shown in FIG. 6, disc 126 is mounted on an end cap member 128, preferably of nylon, together with output terminal 52, and the end cap is mounted on shaft 72 against rotation relative thereto. More particularly in this respect, end cap member 128 includes an apertured hub 130 having axially inner and outer ends, a wall 132 extending radially outwardly of the hub intermediate the ends thereof and a radially outer peripheral wall 134 extending axially inwardly from wall 132 and into a recess 136 provided therefor in the axially outer end of mounting sleeve 96. The axially outer end of hub 130 is provided with a radial aperture which is threaded to receive a set screw 138 by which the end cap is secured to shaft 72 against rotation relative thereto and, thus, against rotation relative to the support stand. As will be appreciated from FIG. 8, disc 126 supporting the secondary winding is secured to the axially inner end of hub 130 of end cap 128 by a plurality of nylon screws 140, whereby disc 126 and the secondary winding are held against rotation relative to shaft 72 and the support stand. As will also be appreciated from FIG. 8, when disc 126 is so mounted, circular conductor 124 is coaxial with axis A and thus with circular conductors 118 and 119 providing primary winding 112. As will be appreciated from FIG. 6, the windings are parallel and closely spaced apart axially from one another. Output terminal 52 is mounted on wall 132 of end cap 128 and is connected to the ends of secondary winding 114 by leads 116 as mentioned hereinabove.

As will be appreciated from the description thus far, storage drum 46, battery B and the inductive coupling component providing primary winding 112 are interconnected for rotation together about shaft 72 and thus axis A while output terminal 52 and the inductive component providing secondary winding 114 are interconnected with shaft 72 and thus the support stand against rotation. Battery B is connected to and has sufficient power to operate camera 24, LED's 26 and modulator 40 for producing a camera output signal which is transmitted through coaxial cable 32 to primary winding 112 of inductive coupling 50, and the latter is operable to inductively transmit the camera output signal to output terminal 52 through secondary winding 114. As shown in FIG. 1, output terminal 52 is adapted to be coupled to camera signal receiving unit 14 through a length of coaxial cable 142 having one end connected to terminal 52 and the other end connected to the receiving unit. In the embodiment illustrated, receiving unit 14 includes a television receiver 144 and a video tape recorder 146. Signal receiving unit 14 can be battery operated and/or provided with a power line 148 for connecting the receiving unit to a standard 120 volt outlet. Battery operation enhances portability, of the apparatus in facilitating its operation in areas where a 120 volt power supply is not readily or conveniently available.

In use, presuming the apparatus to have been carried to the site where a pipe is to be inspected, the operator connects output terminal 52 to receiving unit 14 by means of coaxial cable 142 and, if not battery operated, plugs the receiving unit into a source of power therefor and turns the receiving unit on. Preferably, the operator then withdraws the camera a length of coaxial cable 32 from cable drum 46 and connects battery B to the camera unit by turning on switch 110. At this point, LED's 26 are energized and the operator can check that the camera is working by observing television monitor 144 while scanning the camera relative to an object in the vicinity of the inspection site. The operator then introduces the camera into the pipe to be inspected and manually pushes the coaxial cable into the line to move the camera therealong. The LED's illuminate the interior of the pipe, and the operator can continuously view the interior of the pipe as the camera is moved therealong by observing the camera monitor. The camera output signal is transmitted to the monitor continuously, including any time during which storage drum 46 and thus primary winding 112 of inductive coupling 50 is rotating in response to withdrawal or extension of the coaxial cable from the cable drum. The operator can continuously record the inspecting operation through the use of video tape recorder 146 or, alternatively can use the latter to selectively record portions of the operation. When the inspecting operation is completed, the operator withdraws the camera from the pipe by manually retracting cable 32 and coiling the latter inside the cable drum, and the operator can of course turn off the power supply from battery B and the power supply to receiving unit 14 either prior to, during or following completion of the withdrawal of the camera from the pipe.

While considerable emphasis has been placed herein on the structure and operation of the embodiment herein illustrated and described, it will be appreciate that other embodiments of the invention can be made and that changes can be made in the disclosed embodiment without departing from the principles of the invention. Accordingly, it is to be distinctly understood that the foregoing descriptive matter is to be interpreted merely as illustrative of the present invention and not as a limitation.

I claim:

1. Apparatus for inspecting the interior of a pipe comprising, a camera, a battery, means including cable means electrically connecting said battery and said camera for operating said camera to produce a camera output signal through said cable means to an end thereof spaced from said camera, cable storage means, support means supporting said cable storage means for rotation in opposite directions about an axis for extending and retracting said camera relative to said cable storage means, said end of said cable means and said battery being supported on said cable storage means for rotation therewith, camera output signal terminal means on said support means for connecting said camera output signal to receiving means, and means including relatively rotatable signal coupling means for transmitting said camera output signal from said end of said cable means to said terminal means.

2. Apparatus according to claim 1, and camera monitor means connected to said terminal means for receiving said camera output signal.

3. Apparatus according to claim 2, wherein said camera monitor means includes video receiver means.

4. Apparatus according to claim 3, wherein said video receiver means includes a television receiver.

5. Apparatus according to claim 3, wherein said video receiver means includes a video tape recorder.

6. Apparatus according to claim 1, wherein said camera is a television camera and said means electrically connecting said battery and said camera includes means to convert said camera output signal to a radio frequency signal.

7. Apparatus according to claim 6, wherein said signal coupling means includes first and second inductively coupled conductor means.

8. Apparatus according to claim 7 wherein said first signal conductor means is circular and connected to said end of said cable means and said second signal conductor means is circular and connected to said terminal means.

9. Apparatus according to claim 8, wherein said first and second signal conductor means respectively have first and second diameters, said first and second diameters being equal, and said first and second signal conductor means being coaxial with and axially spaced apart relative to said axis.

10. Apparatus according to claim 1, wherein said camera has a front end, and illuminating means supported adjacent said front end.

11. Apparatus according to claim 10, wherein said illuminating means includes light emitting diodes.

12. Apparatus according to claim 1, wherein said support means includes a stand having axially opposite sides with respect to said axis and a shaft extending between and secured to said axially opposite sides, said shaft providing said axis, and said cable storage means being supported on said shaft for rotation relative thereto.

13. Apparatus according to claim 12, wherein said stand includes handle means for carrying said apparatus.

14. Apparatus according to claim 12, wherein said cable storage means includes an annular housing having spaced apart axially opposite sides and a radially outer peripheral wall therebetween, said cable means being coiled in said annular housing between said sides and said outer wall, and one of said sides having an opening therethrough for extending and retracting said cable means relative to said annular housing.

15. Apparatus according to claim 14, wherein said annular housing includes hub means extending from the other of said opposite sides toward said one of said sides, said hub means including an opening therethrough receiving said shaft, and said opening through said one of said sides being coaxial with said axis.

16. Apparatus according to claim 15, wherein said stand includes handle means for carrying said apparatus.

17. Apparatus according to claim 14, wherein the other of said opposite sides of said annular housing has an outer side, said end of said cable means and said battery being supported adjacent said outer side.

18. Apparatus according to claim 1, further including housing means enclosing said camera, said cable means being connected to said housing means, and means enclosing said cable means between said housing means and said end of said cable means for protecting said cable means against abrasion.

19. Apparatus according to claim 18, wherein said cable means is flexible transverse to the direction between said housing means and said end, and said means enclosing said cable means is tube means of a material for restraining flexing of said cable means transverse to said direction.

20. Apparatus according to claim 1, wherein said camera is a television camera and said means electrically connecting said battery and said camera includes means to convert said camera output signal to a radio frequency signal, said camera having a front end, illuminating means supported adjacent said front end, said support means including a stand having axially opposite sides with respect to said axis and a shaft extending between and secured to said axially opposite sides, said shaft providing said axis, and said cable storage means being supported on said shaft for rotation relative thereto.

21. Apparatus according to claim 20, and camera monitor means connected to said terminal means for receiving said camera output signal, said camera monitor means including video receiver means.

22. Apparatus according to claim 20, wherein said signal coupling means includes first and second inductively coupled conductor means, said first signal conductor means being circular and connected to said end of said cable means and said second signal conductor means being circular and connected to said terminal means, said first and second signal conductor means respectively having first and second diameters, said first and second diameters being equal, and said first and second signal conductor means being coaxial with and axially spaced apart relative to said axis.

23. Apparatus according to claim 20, wherein said cable storage means includes an annular housing having spaced apart axially opposite sides and a radially outer peripheral wall therebetween, said cable means being coiled in said annular housing between said sides and said outer wall, one of said sides having an opening therethrough for extending and retracting said cable means relative to said annular housing, the other of said opposite sides of said annular housing having an outer side, and said end of said cable means and said battery being supported adjacent said outer side.

24. Apparatus according to claim 20, further including housing means enclosing said camera, said cable means being connected to said housing means, and means enclosing said cable means between said housing means and said end of said cable means for protecting said cable means against abrasion.

25. Apparatus according to claim 20, wherein said signal coupling means includes first and second inductively coupled conductor means, said first signal conductor means being circular and having a first diameter and being connected to said end of said cable means, said second signal conductor means being circular and having a second diameter equal to said first diameter and being connected to said output signal terminal means, said first and second conductor means being coaxial with and axially spaced apart relative to said axis, said cable storage means including an annular housing having spaced apart axially opposite sides and a radially outer peripheral wall therebetween, said cable means being coiled in said annular housing between said sides and said outer wall, one of said sides having an opening therethrough for extending and retracting said cable means relative to said housing, the other of said opposite sides of said annular housing having an outer side, and said end of said cable means and said battery being supported adjacent said outer side.

26. Apparatus according to claim 25, further including housing means enclosing said camera, said cable means being connected to said housing means, and means enclosing said cable means between said housing means and said end of said cable means for protecting said cable means against abrasion.

27. Apparatus according to claim 26, and camera monitor means connected to said terminal means for receiving said camera output signal, said camera monitor means including video receiver means.

28. Apparatus according to claim 26, wherein said stand includes handle means for carrying said apparatus.

29. Apparatus for inspecting the interior of a pipe comprising, a length of coaxial cable having first and second ends, a storage drum for said cable, a stand including means supporting said drum for rotation in opposite directions relative to said stand about an axis, said first end of said cable being supported on said drum for rotation therewith, said second end of said cable being extendable and retractable relative to said drum, camera housing means having front and rear ends, said second end of said cable being attached to said rear end, a television camera in said housing means adjacent said front end, means electrically connecting said camera and said second end of said cable, a battery mounted on said storage drum for rotation therewith, means electrically connecting said battery and said first end of said cable for operating said camera to produce a camera output signal through said cable to said first end thereof, said means electrically connecting said camera and said second end of said cable including means for converting said camera output signal to a radio frequency signal, first signal conductor means electrically connected to said first end of said cable and mounted on said drum for rotation therewith, second signal conductor means mounted on said stand in inductively coupled relationship to said first conductor means, camera output signal terminal means on said stand, and means electrically connecting said terminal means and said second conductor means.

30. Apparatus according to claim 29, and video receiver means connected to said terminal means for receiving said camera output signal.

31. Apparatus according to claim 29, and illuminating means in said camera housing means adjacent said front end thereof.

32. Apparatus according to claim 29, and means enclosing said cable between said first and second ends thereof for protecting said cable against abrasion and reinforcing said cable against flexure transverse to the direction between the ends thereof.

33. Apparatus according to claim 29, wherein said stand includes a carrying handle.

34. Apparatus according to claim 29, wherein said drum includes axially spaced apart side walls, one of said side walls having an axially outer side, a sleeve of polymeric material mounted on said outer side coaxial with said axis, said sleeve being rotatable with said drum and having a radially outer side, and battery mounting means on said radially outer side for mounting said battery on said sleeve adjacent said outer side of said one of said side walls.

35. Apparatus according to claim 34, wherein each said first and second signal conductor means is circular, means for mounting said first signal conductor means on said sleeve coaxial with said axis, and means for mounting said second signal conductor means on said stand coaxial with said axis and axially spaced from said first signal conductor means.

36. Apparatus according to claim 35, wherein said sleeve has an axially outer end spaced from said outer side, said means for mounting said second signal conductor means on said stand including a cap member of polymeric material having an end wall spaced from said outer end and transverse to said axis and a radially outer peripheral wall extending axially from said end wall toward said outer end and into axially overlapping relationship therewith.

37. Apparatus according to claim 36, wherein said stand includes axially spaced apart support members and said means supporting said drum for rotation includes a drum shaft fixed to said support members against rotation relative thereto, said drum being supported on said shaft for rotation relative thereto, and said cap member being mounted on said shaft against rotation relative thereto.

38. Apparatus according to claim 37, wherein said camera output signal terminal means is mounted on said end wall of said cap member.

39. Apparatus according to claim 37, wherein said drum includes a hub extending from said one of said side walls toward the other side wall and having an end spaced from said one side wall, said hub having a bore therethrough receiving said shaft, said drum further including a radially outer peripheral wall between said side walls, said cable being coiled in said drum between said side walls and said peripheral wall, and said other side wall extending radially inwardly from said peripheral wall and having a radially inner peripheral edge spaced from said hub to provide an opening for extending and retracting said cable relative to said drum.

40. Apparatus according to claim 36, wherein said means for mounting said first signal conductor means includes a first planar plate of insulating material, said first signal conductor means being a metal clad on said first planar plate, said means for mounting said second signal conductor means includes a second planar plate of insulating material, said second signal conductor means being a metal clad on said second planar plate, said first planar plate being mounted on said axially outer end of said sleeve, and said second planar plate being mounted on said cap member axially inwardly of said end wall.

41. Apparatus according to claim 40, wherein said sleeve includes a mounting plate axially inwardly of said outer end thereof and transverse to said axis, said first end of said cable being attached to said mounting plate, and said camera output signal terminal means being mounted on said end wall of said cap member.

42. Apparatus according to claim 36, and illuminating means in said camera housing means adjacent said front end thereof.

43. Apparatus according to claim 42, and means enclosing said cable between said first and second ends thereof for protecting said cable against abrasion and reinforcing said cable against flexure transverse to the direction between the ends thereof.

44. Apparatus according to claim 43, wherein said stand includes a carrying handle.

45. Apparatus according to claim 36, wherein said stand includes axially spaced apart support members and said means supporting said drum for rotation includes a drum shaft fixed to said support members against rotation relative thereto, said drum being supported on said shaft for rotation relative thereto, said cap member being mounted on said shaft against rotation relative thereto, said means for mounting said first conductor means including a first plate of insulating material supporting said first signal conductor means, said means for mounting said second conductor means including a second plate of insulating material supporting said second signal conductor means, said first plate being mounted on said axially outer end of said sleeve means, and said second plate being mounted on said cap member axially inwardly of said end wall.

46. Apparatus according to claim 45, and illuminating means in said camera housing means adjacent said front end thereof.

47. Apparatus according to claim 46, and means enclosing said cable between said first and second ends thereof for protecting said cable against abrasion and reinforcing said cable against flexure transverse to the direction between the ends thereof.

48. Apparatus according to claim 29, and illuminating means in said camera housing means adjacent said front end thereof, and means enclosing said cable between said first and second ends thereof for protecting said cable against abrasion and reinforcing said cable against flexure transverse to the direction between the ends thereof.

49. Apparatus according to claim 48, and video receiver means connected to said camera output signal terminal means for receiving said camera output signal.

50. Apparatus according to claim 48, wherein said stand includes handle means for carrying said apparatus.

* * * * *